United States Patent
Wernick et al.

(10) Patent No.: US 7,712,901 B2
(45) Date of Patent: May 11, 2010

(54) METHOD AND APPARATUS FOR DIAGNOSING CONDITIONS OF THE EYE WITH INFRARED LIGHT

(75) Inventors: Miles N. Wernick, Chicago, IL (US); Daniel K. Roberts, River Forest, IL (US); Ana S. Lukic, Chicago, IL (US); Yongyi Yang, Westmont, IL (US)

(73) Assignee: Predictek, Inc., Chicago, IL (US)

( * ) Notice: Subject to any disclaimer, the term of this patent is extended or adjusted under 35 U.S.C. 154(b) by 0 days.

(21) Appl. No.: 11/999,529

(22) Filed: Dec. 6, 2007

(65) Prior Publication Data

US 2008/0137034 A1    Jun. 12, 2008

Related U.S. Application Data

(60) Provisional application No. 60/873,669, filed on Dec. 8, 2006.

(51) Int. Cl.
*A61B 3/10* (2006.01)
*A61B 3/14* (2006.01)

(52) U.S. Cl. .................. 351/221; 351/205; 351/210

(58) Field of Classification Search ......... 351/205–206, 351/210, 218, 221
See application file for complete search history.

(56) References Cited

U.S. PATENT DOCUMENTS

2004/0075812 A1*  4/2004  Kardon et al. .............. 351/206
2008/0081996 A1*  4/2008  Grenon et al. .............. 600/443

OTHER PUBLICATIONS

David D. Donaldson, MD "Transillumination of the Iris" Tr. Am. Ophth. Soc., vol. LXXII, 1974.
Matti Saari, MD, et al. "Infrared Transillumination Stereophotography of Normal Iris" Canad J. Ophthal. 12:308, 1977.
M. Saari, et al. "Infra-red transillumination stereophotography of the iris in Fuchs's heterochromic cyclitis" British Journal of Ophthalmology, 1978, 62, 110-115.
Wallace L.M. Alward, MD, et al. "Use of Infrared Videography to Detect and Record Iris Transillumination Defects" Arch Ophthalmol, vol. 108, May 1990.
Daniel K. Roberts, OD, FAAO, et al. "Iris Transillumination Defects in the Pigment Dispersion Syndrome as Detected with Infrared Videography: A Comparison Between a Group of Blacks and a Group of Nonblacks" Optometry and Vision Science, vol. 76, No. 8, Aug. 1999.
William L. Haynes, MD, et al. "Quantitation of Iris Transillumination Defects in Eyes of Patients with Pigmentary Glaucoma" J. Glaucoma, vol. 3, No. 2, 1994.

(Continued)

*Primary Examiner*—Scott J Sugarman
*Assistant Examiner*—Dawayne A Pinkney
(74) *Attorney, Agent, or Firm*—Pauley Petersen & Erickson (57) ABSTRACT

A method and apparatus for imaging an eye of a patient and detecting any condition or disease in the eye. A near infrared light beam is emitted into the eye through the skin adjacent to the eye. A digital image is acquired from the light reflected from the eye. The image shows details that are not perceivable using current examination techniques. Images are acquired using more than one infrared wavelength using a multispectral illumination device for a more thorough analysis.

21 Claims, 6 Drawing Sheets

OTHER PUBLICATIONS

Elzie C. Chan, BA, et al. "Digital Camera System to Perform Infrared Photography of Iris Transillumination" J. Glaucoma, vol. 11, No. 5, 2002.

Daniel K. Roberts, OD, MS "Digital Infrared Photography Assists in the Detection of Iris and Ciliary Body Cysts" J. Glaucoma, vol. 12, No. 3, Jun. 2003.

Daniel K. Roberts, OD, MS, et al. "Infrared Imaging Technique may Help Demonstrate Iris Transillumination Defects in Blacks who Show Other Pigment Dispersion Syndrome Clinical Signs" J. Glaucoma, vol. 16, No. 5, Aug. 2007.

Jukka M. Saari, BM, et al. "Digital Infrared Transillumination Imaging of the Iris" Journal of Ophthalmic Photography, vol. 27, No. 1, Spring 2005.

* cited by examiner

METHOD AND APPARATUS FOR DIAGNOSING CONDITIONS OF THE EYE WITH INFRARED LIGHT

CROSS REFERENCE TO RELATED APPLICATION

This application claims the benefit of U.S. provisional patent application Ser. No. 60/873,669, filed on 8 Dec. 2006. The provisional patent application is hereby incorporated by reference herein in its entirety and is made a part hereof, including but not limited to those portions which specifically appear hereinafter.

BACKGROUND OF THE INVENTION

This invention relates generally to a method and apparatus for diagnosing eye conditions or diseases.

There are many disorders that affect the iris, which is the pigmented structure at the front of the eye. One such disorder is pigment dispersion syndrome (PDS), a disorder that is characterized by a mechanical debridement of pigment from the back surface of the iris. As a result of PDS, pigment granules are deposited on structures within the anterior segment of the eye, most importantly the trabecular meshwork (the structure within the eye that permits drainage). Prolonged deposition of pigment granules in this structure may cause a reduction in the ability of the trabecular meshwork to transport fluid from the eye, which can result in an elevation of the intraocular pressure and glaucoma.

Glaucoma is a frequent complication of the condition, with estimates for the progression from PDS to pigmentary glaucoma ranging as high as 50%. Pigmentary glaucoma is now generally considered as one of the more-common forms of secondary glaucoma.

For the eye care practitioner, visual evaluation of the iris using visible-light transillumination is an important and fundamental technique that is used routinely by optometrists and ophthalmologists in their daily practice. However, the value of this technique is severely limited by the low transmission coefficient of the iris and skin for light in the visible regime. For example, PDS is a fairly common condition. Using conventional examination techniques, PDS has been fond in 2.45% of caucasians undergoing glaucoma screening. However, the true prevalence is probably much greater than this because mild presentations go undetected by traditional examination methods. It has been widely assumed that PDS is very rare in black patients; however, recent research has shown that this observation is probably due to the poor sensitivity of standard diagnostic methods, especially for patients having dark eyes and/or skin, which can severely limit visible-light transillumination.

Traditionally, iris evaluation has been performed with the room lights turned off and the patient positioned with his or her head in front of a slit lamp biomicroscope, which is an instrument used to examine the eye visually under magnification. With the patient looking straight ahead, a small beam of light is directed into the eye through the pupil. The practitioner then visually evaluates the front side of the iris for penetration of reflected light from inside the eye. Normally the iris is fairly opaque and reflected light will not be observed. However, the diseased iris may be thinned in some areas due to loss of pigment granules or tissue atrophy, and thus may permit light to penetrate.

In an alternative method, which is typically performed without the aid of a slit lamp biomicroscope, a fiber-optic light source is placed against the lower eyelid and directed toward the globe of the eye. As in the above method, with the room lights off, the practitioner visually examines the front side of the iris for evidence of penetration by internally reflected light. This second method suffers from the same limitations as the first method.

Both of these methods are somewhat useful in routine practice. However, their success is limited by the low contrast of the features that are observed, which is especially problematic for patients with brown eyes and/or dark skin, or in cases when the disease is subtle or in an early stage of progression. In these situations, the reflected visible light may not penetrate the iris tissue even though iris atrophy and/or pigment granule loss is present. Thus, thinned areas may not be appreciated.

Currently, there are no devices available to the clinician for routine imaging or automated detection of iris defects. There is thus a need for a relatively inexpensive and simple device for use in routine clinical use. There is also a need for a device that records the analysis for tracking of disease progression.

SUMMARY OF THE INVENTION

A general object of the invention is to provide an improved method and apparatus for examining and diagnosing conditions of the eye.

A more specific objective of the invention is to overcome one or more of the problems described above.

The general object of the invention can be attained, at least in part, through a method of detecting a condition or disease in an eye of a patient. The method includes: emitting at least one light beam into the eye through skin directly adjacent to a portion of the eye; digitally capturing a first reflected light spectrum from the eye from the at least one light beam; digitally capturing a second reflected light spectrum from the eye from the at least one light beam; producing a first digital image from the first reflected light spectrum; and producing a second digital image from the second reflected light spectrum.

The invention further comprehends a method of detecting a condition or disease in an eye of a patient including: emitting infrared light into the eye through skin directly adjacent to a portion of the eye; digitally capturing reflected light from the eye; and producing a digital image of the eye using only the digitally captured infrared light.

The invention still further comprehends an apparatus for use in diagnostic imaging of an eye. The apparatus includes a body and an infrared light source in combination with the body. The infrared light source emits one or more spectral ranges of infrared light concentrated around a predetermined infrared wavelength. The body including a light discharge end having a size and shape adapted to be placed against skin adjacent to and over a portion of the eye.

The apparatus of this invention is a new diagnostic imaging device for use by eye care practitioners. The apparatus collects and, desirably, automatically analyzes multispectral infrared images (e.g., multiple images, each taken using a different wavelength of light) of the iris (the pigmented structure at the front of the eye), permitting the visualization and automatic detection of iris defects associated with pigment dispersion syndrome (PDS) and other ocular conditions that can lead to glaucoma. The multispectral imaging according to this invention produces useful, quality images in spite of complicating variations in eye and skin pigmentations of patients. Multispectral imaging also permits abnormalities to be detected by virtue of different appearances at different wavelength spectra.

In a preferred imaging method, narrowband near-infrared (NIR) light is directed through the skin above the cheekbone, thus causing the eye to glow from within. Some of this light penetrates the iris from behind, permitting details of iris structures to be imaged. Multiple images can be acquired in rapid succession at different wavelengths across the NIR band. These images will be automatically analyzed by computer to identify abnormal regions, with capabilities for longitudinal monitoring to track disease progression.

Whereas iris defects show very limited contrast when transilluminating the iris with visible light, these defects are clearly visualized when using NIR light. The imaging technique of this invention can readily detect iris defects that are difficult or impossible to observe by visual examination, even in patients with darkly pigmented eyes and/or skin for whom traditional examination techniques perform very poorly. The multispectral capability of the apparatus allows adaptive optimization of imaging performance to each subject's pigmentation type, and the spectral signatures within the images can be used to help discriminate defects from normal iris tissue.

As used herein, references to "infrared" are to be understood to refer to include near infrared wavelengths.

References herein to "transillumination" are to be understood to refer to the illumination of an object, e.g., an eye, by passing light through it, rather than by reflecting light from its surface.

References herein to "multispectral" are to be understood to refer to more than one light wavelength spectrum.

Other objects and advantages will be apparent to those skilled in the art from the following detailed description taken in conjunction with the appended claims and drawings.

DETAILED DESCRIPTION OF THE INVENTION

The present invention provides a method of detecting a condition or disease in an eye. The method of this invention utilizes a light source, desirably including infrared (IR) light, and more desirably including narrow-band infrared light (NIR), directed through the skin above the cheekbone. Applied in this manner, the light causes the eye to glow from within. Some of this light is reflected out of the eye and penetrates the iris from behind, permitting details of iris structures to be digitally imaged. In one embodiment of this invention, predetermined wavelengths of light, e.g., IR light, are sequentially emitted into the eye through the skin, thereby allowing for digital imaging of the eye at more than one wavelength of IR light. The method of this invention, such as implemented using the apparatus described below, allows for multiple images to be acquired in rapid succession, each image at one of the different wavelengths across, for example, the NIR band. According to one embodiment of this invention, these images will be automatically analyzed by a data processor to identify abnormal regions, with capabilities for longitudinal monitoring to track disease progression.

The invention also includes an imaging apparatus for assessment of diseases of the iris. The apparatus of this invention includes a light source for transillumination of the eye. The apparatus of one embodiment of this invention also desirably includes a digital image detector for recording images of the eye when the light source is applied. At a minimum, the apparatus of this invention is envisioned to become a standard piece of equipment in eye care practices that concentrates on the management and treatment of glaucoma. However, the apparatus can also be an important research resource that will be used by investigators in university research centers. The method and apparatus of this invention can be used to diagnose and analyze eye diseases or eye conditions, such as pigment dispersion syndrome, iridociliary cysts, albinism, trauma, exfoliation syndrome, Fuchs' heterochromic iridocyclitis, and problems caused by intraocular lens implants.

Figure 1:
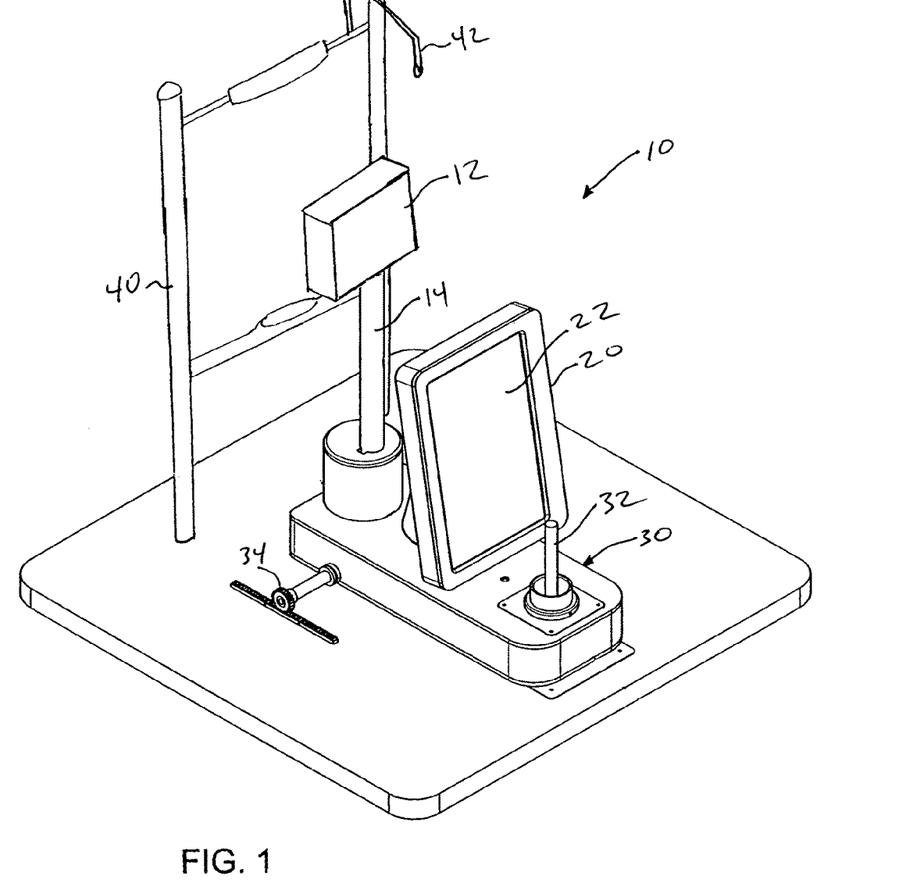
FIG. 1 is a digital image detection system for use in the apparatus of one embodiment of this invention.

FIG. 1 illustrates a digital image detection system 10 for use in the apparatus of this invention. Detection system 10 includes a digital image detector 12 for taking a picture of an eye, and more specifically, for digitally capturing light reflected from within the eye, resulting from a transillumination light source applied to the eye. The digital image detector 12 can be any digital detector, and is selected based upon its ability to detect and image the type of light reflected from the eye. For example, when infrared light is used as the light source, the digital detector 12 desirably detects infrared light in order to produce digital images, such as in combination with a data processor, using the detected infrared light. Various commercial digital cameras, for example those modified to remove any IR-blocking filter, could be used as the digital detector 12, and the detection system 10 can be adapted to secure a digital camera on detector stand 14 by the screw-mount hole commonly found on most cameras.

In the system 10 shown in FIG. 1, the digital image detector 12 is connected to a user interface 20. The user interface 20 includes a view screen 22 for viewing images produced using the digital image detector 12. Desirably, the view screen 22 includes a touch screen to allow user interaction with the display, and control of at least portions of the system thereby. The digital image detector 12 can be connected directly to the user interface 20, but desirably a data processor, e.g., computer, is used as an intermediary for analyzing and transmitting the images to the view screen 22. Alternatively, the system 10 could exclude the user interface 20, and be used with a user's existing computer, e.g., a desktop or laptop, whereby the digital images are shown on the associated monitor. The system 10 desirably includes a recordable medium for recording and storing the digital images. The recordable medium can be included in the detector 12 itself, within the user interface 12, or with or within a data processor used with the system 10.

The detection system 10 further includes a control device 30 which allows the detector 12 to be moved into the proper position once the patient's head is positioned on the adjustable chin/headrest 40. The control device 30 in FIG. 1 includes a joystick 32 for moving the detector 12 into position. The joystick 32 allows the camera to be moved freely from side to side, and forward/backward to control the focus and field of view of detector 12. The joystick 32 is connected to a system of gears, such as gear 34, and other mechanical components, according to known mechanisms, to move the detector into the desired positioning. The joystick 32 can include a trigger to activate the detector 12 to capture an image. As will be appreciated by those skilled in the art following the teachings herein provided, various and alternative sizes, shapes, and configurations are available for the detection system and apparatus of this invention. For example, in one embodiment, an optional footswitch is provided for triggering the start of image acquisition. The footswitch frees the clinician's hands to apply the light source and position the camera. Further, an optional fixation/constriction light source 42 can be directed at the eyes and used to help the patient to look forward, and to create consensual papillary constriction in the examined eye so that the iris surface area is maximized.

Figure 2:
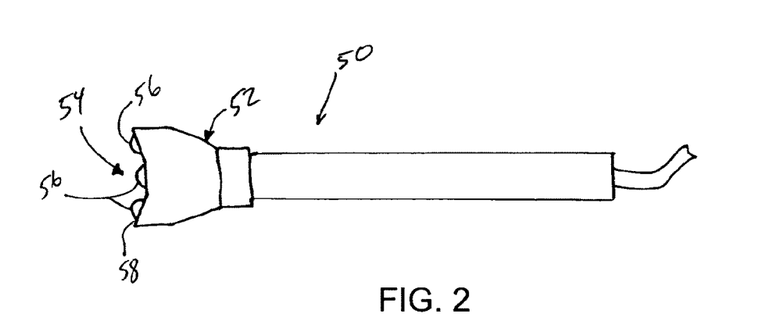
FIG. 2 is an illumination device according to one embodiment of this invention.

The detection system 10 is desirably used in combination with a transillumination device for introducing a beam of light into a patient's eye through the skin directly adjacent to and over a portion of the eye. FIG. 2 illustrates a transillumination device 50, according to one embodiment of this invention. Device 50 includes a body 52 and a light source 54. The light source 54 can include any desirable light source, and in the embodiment of this invention shown in FIG. 2, is a narrow band infrared light source.

Various sources of narrowband illumination are available for use with the method and apparatus of this invention, such as light emitting diodes (LEDs), laser diodes (LDs), and filtered white light. The infrared light source 54 of FIG. 2 includes three light emitting diodes 56. LEDs provide an ideal light source for use in this invention because they offer sufficient power, they are inexpensive, they are totally safe, they can be switched electronically, and they are available in a wide variety of wavelengths, such as 625 nm, 655 nm, 700 nm, 750 nm, 810 nm, 850 nm, 910 nm, 950 nm, 1000 nm, and 1050 nm.

The shortest of the above wavelengths (625 nm and 655 nm) are not as effective for iris transillumination due to high absorption and scattering by the skin. The longest of the above wavelengths (e.g., 1000 nm and 1050 nm) generally show poor contrast of ITD features relative to other structures. Thus, in one preferred embodiment of this invention, the light source includes LEDs that each emits only one or more spectral ranges of light concentrated around a predetermined wavelength selected from wavelengths from about 650 nanometers to about 1000 nanometers. Exemplary infrared LED wavelengths include 700 nm, 750 nm, 810 nm, 850 nm, 910 nm and 950 nm. Also, as will be appreciated, although a LED may emit light concentrated at its identified wavelength, the LED is likely to emit wavelengths in a spectral range near to the identified peak wavelength.

Referring again to the device 50 in FIG. 2, each of the three LEDs 56 has the same selected wavelength, e.g., 750 nm. Thus, for multispectral imaging at more than one different wavelengths, more than one transillumination device would be needed. The transillumination device 50 is desirably controlled by an electronic control module in combination with the data processor, which allows the intensity to be varied or switched individually from a software interface.

The three LEDs 56 are arranged in a linear fashion at a light discharge end 58 of the body 52. The light discharge end 58 has a size and shape adapted to be placed against skin adjacent to and over a portion of the eye. Desirably, the light discharge end 58 has a shape with a first dimension that is greater than a second dimension, such as rectangular, elliptical, or ovoid. When in use, the light discharge end 58 is desirably positioned at the anterior of the lower eyelid. The elongated profile of the light discharge end 58 ensures that the clinician holds the probe roughly normal to the globe of the eye, at least with respect to the horizontal plane.

Figures 3, 4, 5:
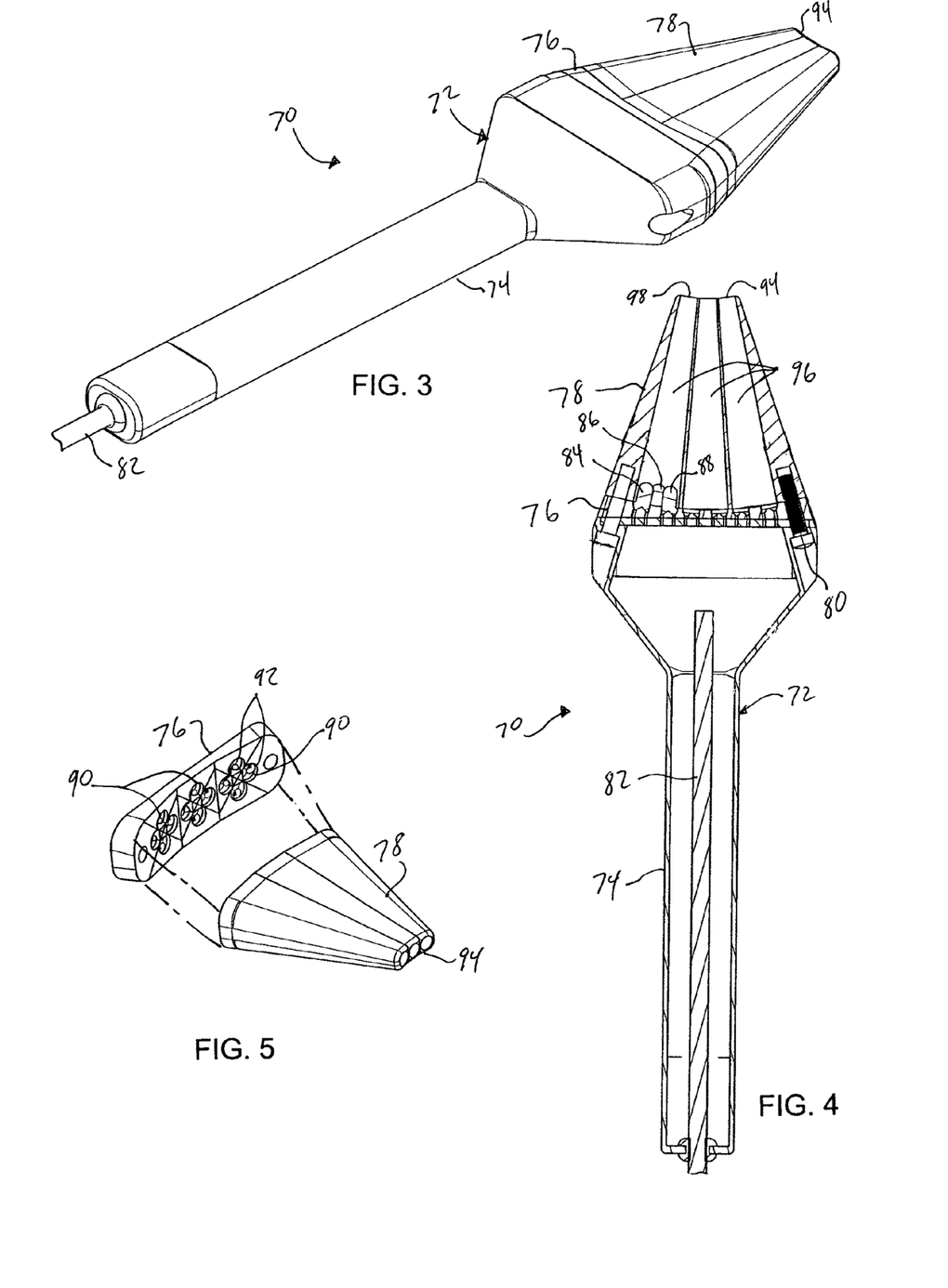
FIGS. 3-5 illustrate an illumination device according to one embodiment of this invention.

FIGS. 3-5 illustrate a transillumination device 70 according to another embodiment of this invention. The device 70 includes a body 72. The body 72 shown in FIGS. 3-5 includes a handle 74, an electric socket element 76 and a light focusing element 78. The electric socket element 76 and the light focusing element 78 are attached to the remainder of the body 72 by a bolt or screw 80. A wire 82, connectable to a power source (not shown), extends through the handle 74 and is in electric power supplying connection with the electric socket element 76. As will be appreciated, various sizes, shapes, and configurations are available for the body, handle, electric socket element, and light focusing element of this invention. For example, the electric socket can be integrally formed with the body, and/or the illustrated elongated handle may be substituted with a wider, or perhaps round, body that can be held in the clinician's hand.

The device 70 includes a light source, shown in FIG. 4 as a plurality of light emitting diodes 84, 86, and 88. As shown in FIG. 5, the electric socket element 76 includes three plug sets 90, each plug set 90 including four electric plugs 90. Each electric plug 92 is adapted to receive a light emitting diode, such as one of light emitting diodes 84, 86, and 88. In one embodiment of this invention, each of the light emitting diodes 84, 86, and 88 emits only one spectral range of infrared light that is concentrated around a predetermined infrared wavelength. For example, diode 84 can be a 700 nm LED, diode 86 can be a 750 nm LED, and diode 88 can be an 850 nm LED.

Including LEDs of different wavelengths in device 70 provides for a multispectral device that is able to generate beams of light concentrated around different desired light wavelengths from a single device. The multispectral device 70 desirably is coupled with an electronic control module (ECM) to provide maximum flexibility of operation to facilitate exploratory studies and optimization of illumination. The ECM allows LEDs of only one or more wavelengths to operate at one time, based upon control signals from the data processor and/or user. The ECM also desirably can adjust the power level of the LEDs individually as well as turning them on or off as desired.

The light focusing element 78 extends from the socket element 76 to a light discharge end 94. The light focusing element 78 includes three light focusing channels 96 extending therethrough, with each light focusing channel 96 associated with and disposed over one of the LED plug sets 90. As shown in FIG. 4, the light focusing element 78 is disposed over the plug sets 90 so that the LEDs are disposed at least partially within the corresponding light focusing channel 96. Desirably, each light focusing channel includes an LED of each desired light wavelength. The light focusing channels 96 are desirably tapered, include a reflective surface, and extend between the light source and the light discharge end, all for focusing the light from the LEDs through a passageway 98 to the light discharge end 94. The light discharge end 94, as discussed above, has a size and shape adapted to be placed against the skin adjacent to and over a portion of the eye. As will be appreciated, various and alternative sizes, shapes, amounts, types, and configurations of the LEDs, the light discharge end, and the light focusing channels are available for this invention.

The device and method of one embodiment of this invention include and are implemented in part by software that is recorded on a recordable medium and executable on a data processor (e.g., a laptop computer). The software controls the operations of the different components of the imaging apparatus of this invention. The entire imaging process can be carried out through interaction with a unified graphical user interface, as discussed above. The software provides an interface for controlling the transillumination light source. The user can select the wavelength to use and adjust its power level through the user interface. The software also provides a set of default power levels based on the race and iris color of the patient. The software further provides an interface for controlling the camera setting: e.g., brightness, contrast, gamma and exposure. The software of one embodiment of this invention also provides a set of default camera settings based on the race and iris color of the patient. The software provides real-time image display on the user interface or associated computer, which the examiner uses to adjust the focus and field of view of the camera. The transillumination images are acquired and recorded by, for example, depressing a footswitch, and the software then displays all acquired images on the screen for visual examination. The software also provides an interface for recording relevant subject information and archiving acquired image data. Image filenames are automatically created using the imaging parameters and unique subject identification code. All images are saved on a recordable medium, such as a hard drive or flash drive, in a suitable image format, such as a bitmap format using lossless compression. Personal identification information is desirably saved separately and kept confidential. The software maintains an image database and provides easy access to archived images. Users can search for a subset of images according to acquisition date, wavelength, patient identification, iris color, race, diagnosis and imaged eye. The list of images satisfying all criteria is desirably shown in a separate window. The user can then view all the images from the list or only selected ones.

The above described apparatus is useful in implementing the method of this invention. Using the transillumination device, such as shown in FIGS. 2 and 3, a light beam is emitted into the eye, desirably through skin adjacent to and over a portion of the eye. The emitted beam is reflected within the eye and causes the eye to glow from within. When the light is in the near infrared band, it appears dim or invisible to the patient, but it is easily detectable by a near infrared CCD camera positioned on the imaging platform. The reflected light is digitally captured and used to produce a digital image of the eye which can be analyzed by a clinician or automatically by the software described above. Desirably the above described steps are repeated using light at different wavelengths, such as sequentially emitted using the multispectral device shown in FIG. 2. Using images produced with more than one wavelength improves the analysis and diagnosis using the images.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

The method of this invention was tested in the clinics of the Illinois Eye Institute (IEI) for acquisition of iris transillumination images of patients. Two groups of subjects were recruited from an existing patient pool at IEI, without preference to age or sex. The first group consisted of 12 Caucasian subjects, of which six were normal and the other six had PDS. The second group consisted of 12 African-American subjects, of which six were normal and the other six had PDS.

All 12 African-American subjects had dark-colored irides (dark brown). Among the Caucasian group, of the six normal subjects, four had blue eyes, one light hazel, and one light brown; of the six PDS subjects, three had blue eyes, one light hazel, two dark brown. These two groups were chosen to determine whether large variations in iris transmission spectra can be accounted for in image acquisition and processing.

These subjects were imaged using an apparatus as described above, in a total of 24 separate imaging sessions. Both eyes of each subject were imaged at each of six wavelengths. For a repeatability study, five of the 12 PDS subjects (three Caucasian and two African-American) were further imaged in repeated sessions.

For testing, six illumination devices, as shown in FIG. 2, were constructed, one for each of the selected wavelengths. For each wavelength the corresponding device was constructed from three identical LEDs (obtained from Roithner Laser), which are controlled by the electronic control module discussed above, allowing their intensity to be varied or switched individually from software. In each device, the three LEDs were arranged in a linear fashion. When in use, the tip of the probe was positioned at the anterior of the lower eyelid.

LEDs producing low radiance levels, but sufficient for testing when used in groups of three, were used. The radiance of present-day LED technology is known to be well within established safety limits under normal viewing conditions. Nevertheless, as a precautionary measure, the thermal retinal exposure was calculated for each light probe based on the spectral characteristics of the LEDs, and their measured power output. The peak exposure level, with all LEDs operating at their maximum rated power level, was well below the hazardous exposure limit by a large margin (one to two orders of magnitude in every case). Each LED had a narrow spectral band centered on its nominal frequency in the NIR region, and consequently posed virtually no blue-light hazard to the retina. For each device, the radiance of each LED assembly was measured by using a Tektronix J16 digital photometer with J6502 irradiance probe, ensuring that no probe could exceed its maximum rated power level.

Furthermore, the exposure levels of the device were benchmarked against a standard illuminator used in routine clinical eye exams (Welch Allyn illuminator with 998079-14 halogen lamp), and found that the exposure levels of the LED devices were only a small fraction of that of the illuminator (all by a factor greater than 5). In other words, the light levels used in the instruments were much lower than in a standard eye exam. In addition, light in the red to NIR range is more comfortable for the patient because it is perceived to be very dim to invisible.

A monochrome CCD camera (Imaging Source DFK 21F04) with VGA resolution (640×480), and spectral sensitivity extending well into the NIR range (up to 1000 nm) was used as a detector. The camera could be programmed to capture up to 30 frames/sec. In addition, it supported the IEEE 1394 communication standard, and was connected to a computer through a firewire interface for data transfer and camera control. The camera was fitted with an 8-mm lens (Edmund MVO® μ-Video™). At this focal length the iris occupies most of the field of view of the sensor array.

To obtain good results, it is important for the patient to look directly forward into the camera. It was also beneficial that the pupil be constricted, so that the iris area is maximized and, thus, most easily visualized. Both goals were achieved by illuminating the fellow eye (the eye not being examined) with a fixation/constriction light, consisting of a red LED (Chicago Miniature Lamp CMD3X50, 150mcd@20mA) on an articulated arm as shown in FIG. 1. During examination, the clinician instructed the patient to look at the light, thus causing the patient to look forward. Illumination of the fellow eye also causes consensual papillary constriction. This permitted constriction of the pupil being examined without the need to illuminate this eye directly (and thus corrupt the image). The LED was housed in a plastic tube in order to further minimize its interference on the eye being imaged. A knob was included for adjusting the intensity of the LED, which the examiner could use to achieve the desired level of papillary constriction during imaging.

Because room light can interfere with imaging, the apparatus of this invention is best used in a darkened room. To help the clinician become oriented and perform coarse positioning of the camera, a bright white LED (Radio Shack 276-230, 1100mcd@20mA) was installed, which illuminated the eye being imaged. This had the added benefit of reducing the amount of time that the light probe is applied to the patient's skin, thus minimizing any discomfort. This general illumination source was turned off during image acquisition.

The image acquisition steps involved were as follows: 1) the chin/headrest and probe were cleaned with an alcohol swab; 2) the subject positioned himself/herself using the chin/headrest apparatus; 3) the camera was coarsely adjusted for focus and field of view by using the general-purpose illumination light; 4) the transillumination light source of the selected wavelength was applied to the lower eyelid of the eye under examination, and directed toward the globe of the eye; 5) the small fixation light source attached to the head rest was directed at the fellow eye to guide the patient looking forward, and to create consensual papillary constriction in the examined eye; 6) the real-time transillumination image of the iris displayed by the computer was examined, and if necessary, the parameters of the camera and transillumination light and image were adjusted for best quality; and finally 7) the images were acquired and saved on the computer by depressing the footswitch.

In summary, each patient was imaged for the following different settings: (2 eyes)×(6 wavelengths). At the end of the imaging session, the acquired images were examined for any inconsistencies (e.g., eye movement, upper eyelid obstruction, etc.). The acquisition was repeated when necessary. The total imaging time was typically around 10-15 minutes per session, due to the use of separate light probes for the different wavelengths. In some patients imaging time was extended because: 1) some subjects had dry eyes causing them to frequently blink during imaging, requiring imaging to be repeated; and 2) the eyes of some subjects were deeply set, and thus extra care was required to obtain an unobstructed view of the iris. Using artificial tear drops or proparacaine HCL 0.5% can improve patient comfort and reduce the image acquisition time significantly.

Figure 6:
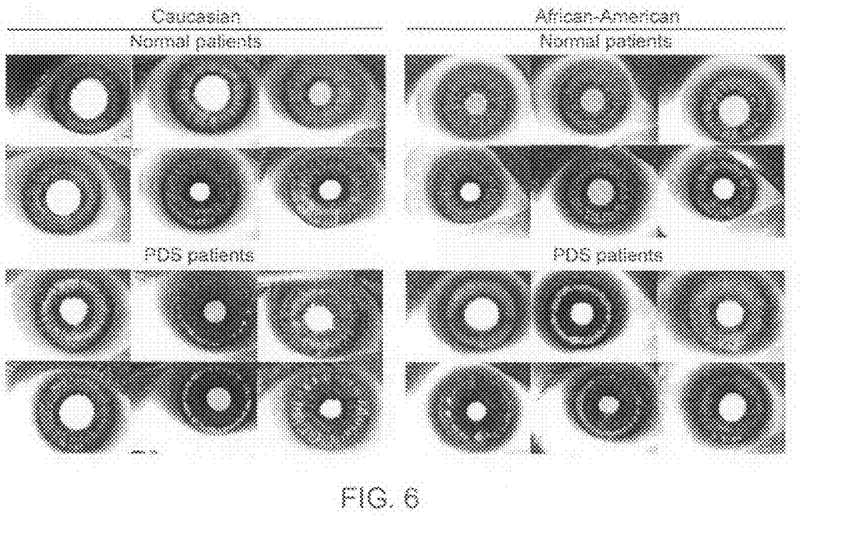
FIG. 6 shows example images, annotated to highlight PDS defects, of normal and PDS patients imaged according to the method of one embodiment of this invention.

FIG. 6 shows example images of normal and PDS patients (one eye of each patient), all collected at a particular wavelength, for both Caucasian (700 nm) and African-American subjects (750 nm). The PDS images show the locations of ITDs identified (ITDs appeared green in the original images) by manually guided image analysis. Optimum ITD detection is obtained by combinations of wavelengths that differ for different skin/eye colors.

Based on past experience, there was a concern that it might be difficult to acquire multispectral iris images in a repeatable fashion, because: 1) the positioning of the transillumination light probe on the eyelid might vary between imaging sessions; 2) the eye under examination may not always look forward, especially for patients with amblyopia (lazy eye); 3) the constriction of the iris might vary between scans; and/or 4) the patient might corrupt the scan by inadvertent eye movement and blinking. However, analyses of the acquired images in our repeated imaging sessions with five PDS subjects (three Caucasian and two African-American) revealed that, with the apparatus and method of this invention, the transillumination features of the iris can be reliably imaged with good repeatability.

Before conducting a statistical analysis of repeatability, a preliminary assessment was performed in which two repeated sets of images from each of the five PDS subjects were visually inspected and compared, and a conclusion was reached subjectively that there was little variation between the two imaging sessions for each subject based on the image features of the transillumination defects.

Next, all the ITD regions of these five repeat PDS subjects were identified and manually outlined. This labeling was done using images from one spectral band (700 nm for Caucasian and 750 nm for African-American). Altogether, a total of 66 ITD regions were identified. Subsequently, these identified ITD regions were manually identified in their corresponding images from other spectral bands. The visibility of these identified ITD regions was then analyzed for the two repeat sessions.

As a measure of the visibility of an ITD region of interest (ROI), we computed its image contrast relative to the surrounding pixels. Specifically, for each identified ITD region, a larger surrounding region was extracted from the image by appending an equal number of immediately neighboring pixels to the ITD ROI. The image contrast of the ITD was then calculated as:

$$C = \frac{\bar{I}_{ROI} - \bar{I}_{surround}}{\bar{I}_{ROI} + \bar{I}_{surround}} \quad (1)$$

where $\bar{I}_{ROI}$ denotes the average image intensity of all the pixels in a ROI, and $\bar{I}_{surround}$ denotes the average image intensity of all the appended surrounding pixels. The use of averages to compute the contrast in Equation (1) reduces sensitivity to outlier pixel values that may result from noise or errors in the manual labeling of the ITDs.

For each identified ITD region in a subject, its contrast values were computed for each of the images acquired with the six spectral bands from each session. The resulting six contrast values were then used to form a feature vector, called the multispectral contrast vector. This contrast vector was also computed for the same ITD region from the images acquired in the repeat session.

Figure 7:
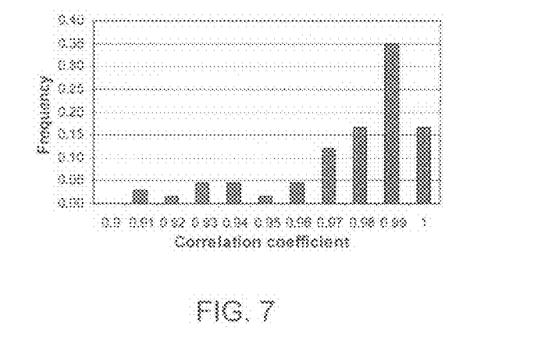
FIG. 7 is a histogram of the calculated correlation coefficients from the examples below.

Next, the correlation coefficient between the two multispectral contrast vectors (corresponding to the two sessions) was computed for each ITD region. FIG. 7 shows a histogram of the calculated correlation coefficients for all the 66 identified ITD regions. It can be seen that for all ROIs the correlation coefficient between the two imaging sessions is greater than 0.90, and for over 50% of the ROIs the correlation coefficient is greater than 0.99. The overall average value of the correlation coefficient is 0.972. These results demonstrate that there is a relatively high degree of consistency between the two imaging sessions for the different subjects.

Figure 8:
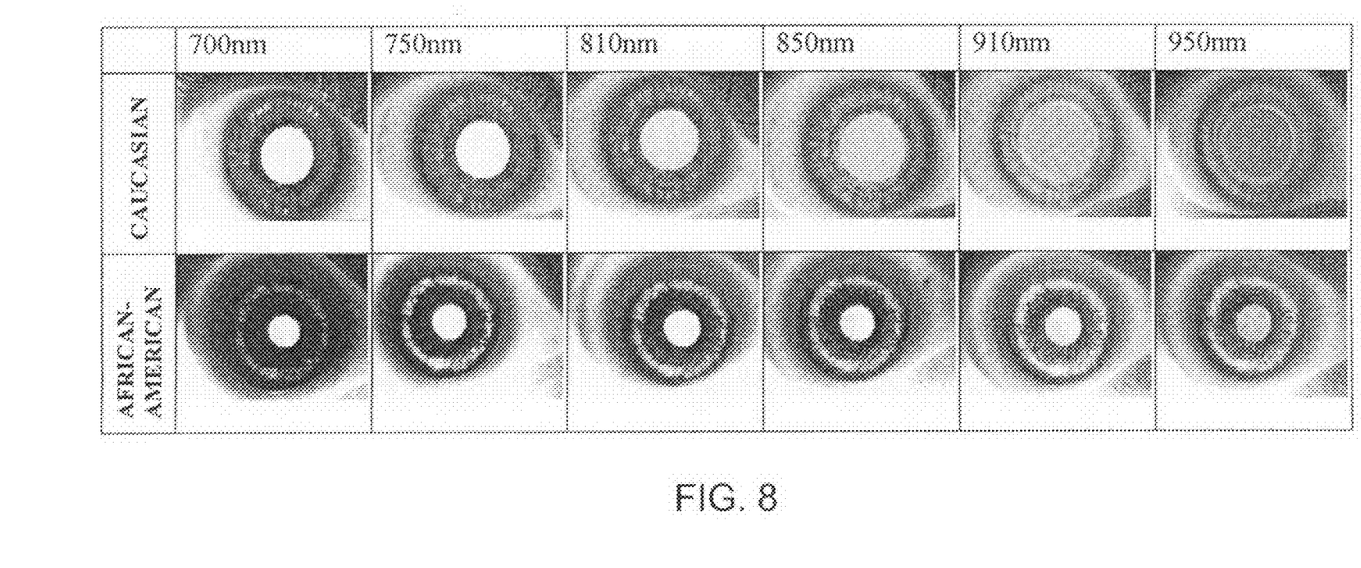
FIG. 8 includes images of the same iris acquired at different wavelengths according to the examples below.

FIG. 8 shows a set of images from a Caucasian subject with blue irides (top row) and an African-American subject with dark brown irides (bottom row) acquired at six different wavelengths. These images show that the visibility of ITDs and of normal structures (which could cause false positives) vary significantly, even over this narrow band of 700-950 nm. In the Caucasian subject, the ITDs are clearly seen near the top and bottom of the iris at 700 nm, but become completely invisible by 950 nm. In this African-American subject, the ITDs show best contrast at about 750 nm. Note that, at longer wavelengths, the African-American subject's image begins to show fine detail of normal iris structures, which could cause false positives in ITD detection. Thus, it became clear that wavelength is an important consideration to obtain optimum results.

Statistical analyses were conducted on the effects of wavelength and subject group on the transillumination images. Once again, the visibility of the ITDs was measured by computing the image contrast. This time, all 12 PDS subjects were used. For this purpose, the ITD regions in the remaining seven PDS subjects (besides the five PDS subjects already used in the repeatability study above) were also identified, and their image contrast values were calculated for all six spectral bands. Altogether a total of 167 ITD regions were identified, with their image contrast calculated for each spectral band.

Figure 9:
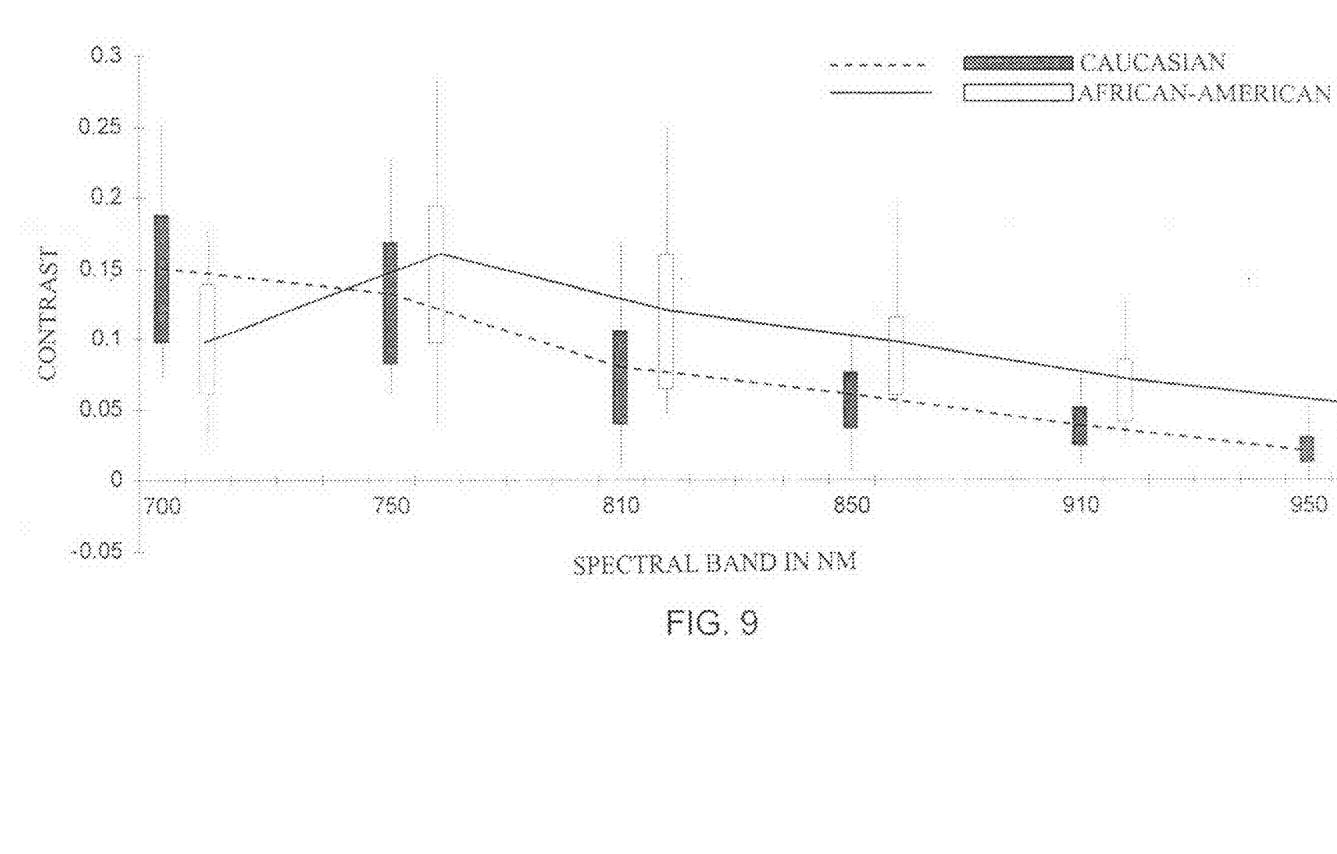
FIG. 9 is a box-whisker plot summarizing contrast values of the examples below.

FIG. 9 summarizes the contrast values of all the 167 ITD ROIs, where the contrast values are grouped according to the wavelength and patient group (Caucasian vs. African-American). In FIG. 9 the profile of the ROI contrasts for each subject group is summarized by a box-whisker plot, in which the box denotes the 25th to 75th percentile range, and the whiskers extend to the 10th and 90th percentile values. Dashed and solid lines signify the average ROI contrast across all spectral bands for Caucasian and African-American groups, respectively.

As can be seen from FIG. 9, the contrast values of the African-American group are generally higher (hence yielding better ITD visibility) than that of the Caucasian group, except at the wavelength 700 nm. For the Caucasian group the best visibility is achieved at 700 nm, while for the African-American group it is achieved at 750 nm. This is consistent with the images in FIG. 8. It is important to note, however, that the results in FIG. 9 also reveal that there are significant variations within each subject group, indicating that there are significant differences among the individual ROIs. Thus, one can infer that the optimal spectral bands might vary among the ROIs within each subject group.

A statistical analysis was also conducted on whether the observed difference in FIG. 9 between the two subject groups is statistically significant. MANOVA (multivariate analysis of variance) was performed on the multispectral contrast values to test whether the observed difference is simply a result of chance (null hypothesis). The test statistic we used for hypothesis testing is the so-called Wilks' lambda defined as:

$$\Lambda = \frac{|W|}{|B+W|} \quad (2)$$

where W is the pooled within-group sum of squares and products (SSP) matrix and B is the between-group SSP matrix. For the distribution of $\Lambda$ under the null hypothesis, Bartlett's approximation was used. MANOVA analysis of the data yielded $\Lambda=0.011$, based on which it was concluded that the observed difference between the two subject groups was highly statistically significant. The p-value was determined to be almost zero ($p<10^{-8}$).

To identify the best spectral bands for ITD detection, statistical analyses were performed of the saliency (discrimination power) of multispectral image features for ITDs identification. The approach was to identify the spectral bands, or linear combination of them, that could offer the best discrimination of ITDs from normal iris regions. This study also provided the necessary confirmation of the feasibility of developing an automated approach for detection of ITDs.

In the saliency analyses, the identified ITDs in the 12 PDS subjects were compared against a number of normal iris regions that were selected from the 12 normal subjects. The multispectral contrast vectors were then computed for both the ITD and normal ROIs. Next a statistical pattern recognition algorithm was used to investigate how well the ROIs from the two classes (i.e., ITD vs. normal) can be discriminated based on the multispectral contrast vector. The goal was to analyze the saliency of each spectral band, i.e., its importance to successful discrimination.

In the selection of normal ROIs, care was taken that they would resemble the profile of ITDs. For this purpose, the profile of the identified ITD regions were first analyzed based on the following geometric properties: area, aspect ratio, orientation, and position within the iris. ROIs were then extracted from the normal iris subjects, so that their profile matched that of the ITDs. Specifically, for each subject, the number of regions was first selected (on the condition that the average number of ROIs per image was the same as that of ITDs); then the geometric parameters for each region was selected according to their corresponding distributions derived from the ITD regions. An elliptical region in the normal iris was then selected according to the selected parameters.

The linear support-vector machine, a modern machine-learning algorithm, was then used to investigate how well the ROIs from the two classes (i.e., ITD vs. normal) can be discriminated by the multispectral contrast vector. A split-half resampling procedure was used to train and evaluate the classifier. In this process, the ROI feature samples were systematically divided into halves, with each half being assigned in turn for training and testing. Since the results of MANOVA analysis showed that there was a significant difference between the African-American and Caucasian subject groups, the discrimination power of the spectral bands for these two groups was accordingly analyzed separately.

The next step was determining the optimal subset of bands for discrimination. Optimality was defined as the rate of correct classification of ROIs on the 400 test sets generated by a split-half resampling procedure. Because there were only six bands to consider, there were only 63 ways to form distinct subsets of bands (6 subsets having one band, 15 subsets having 2 bands, etc.). Therefore, an exhaustive search of all possible subsets of bands was feasible, and would ensure that the global optimum subset was found.

Table 1 summarizes the findings of this experiment. For both patient groups, two bands provided best discrimination. For the Caucasian patients, the combination of 700 nm and 750 nm performs best. For the African-American patients, it was the combination of 810 nm and 850 nm. Interestingly, the African-American patients, who are typically the most difficult to diagnose using visual examination, were easier to diagnose than Caucasian patients when using two NIR bands.

TABLE 1

Combinations of spectral bands for ITD discrimination

| | Correct classification rate | Spectral bands | | | | | |
|---|---|---|---|---|---|---|---|
| | | 700 nm | 750 nm | 810 nm | 850 nm | 910 nm | 950 nm |
| Caucasian | 94.6% | • | • | | | | |
| African-American | 99.1% | | | • | • | | |

Figure 10:
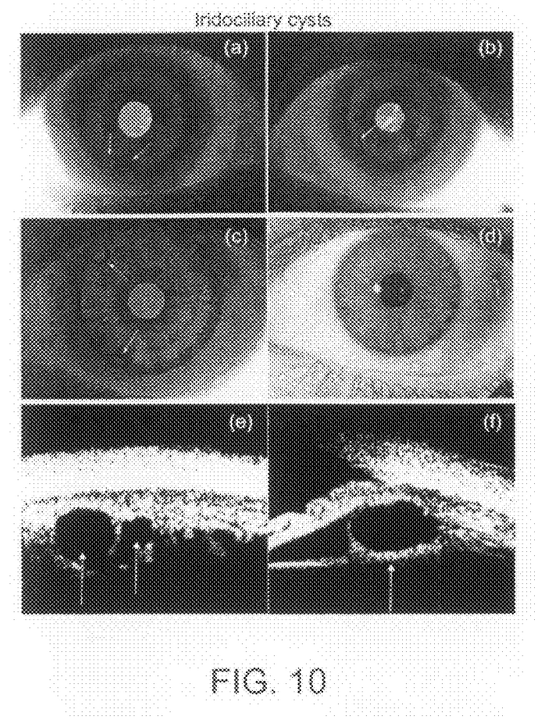
FIG. 10 includes iris images showing iridociliary cysts detected with a method of one embodiment of this invention in normal patients who were unsuspected of having the condition after examination.
Figure 11:
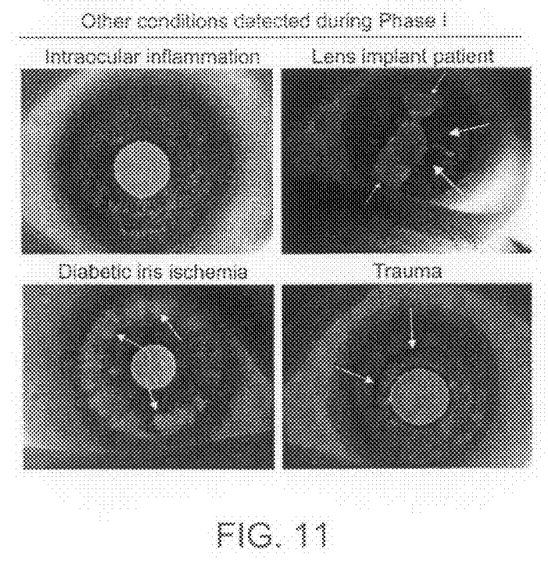
FIG. 11 includes iris images showing conditions detected with a method of one embodiment of this invention in normal patients who were unsuspected of having the condition after examination.

It is also important to note that previously undetected conditions in particular patients were identified during the above testing. During the course of the project, some of the research subjects were found to have iridociliary cysts, signs of trauma, problems caused by an intraocular lens implant, and other conditions. FIG. 10 shows iridociliary cysts in two subjects, neither of which was suspected to have cysts until NIR iris imaging was performed. The condition was confirmed by high-resolution ultrasound images (FIG. 10, bottom row). Noninvasive NIR imaging according to this invention is thus potentially a quick, reliable, and inexpensive method to detect these cysts. FIG. 11 shows images of patients with intraocular inflammation (upper left), problems caused by a lens implant (upper right), iris ischemia (lower left), and prior trauma (lower right), each showing a clearly anomalous iris image. None of these defects were observed during visual examination.

Thus, the invention provides a method and apparatus for diagnosing and analyzing eye conditions and/or diseases. The apparatus according to this invention is relatively easy to use; with a few minutes of training, a technician should be able to successfully and repeatably image a patient with no difficulty, with very few occasions requiring repeat scans. Also, the instrument produces outstanding sensitivity, even of very dark-colored irides.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method of detecting a condition or disease in an eye of a patient, the method comprising:
    emitting a first light beam into the eye through skin directly adjacent to a portion of the eye to illuminate the iris of the eye from within the eye, the first light beam having a first light spectrum;
    emitting a second light beam into the eye through the skin directly adjacent to the portion of the eye to illuminate the iris of the eye from within the eye, the second light beam having a second light spectrum that is different from the first light spectrum;
    digitally capturing a first light spectrum penetrating the iris from the first light beam within the eye;
    digitally capturing a second light spectrum penetrating the iris from the second light beam within the eye;
    producing a first digital image of the iris from the first light spectrum;
    producing a second digital image of the iris from the second light spectrum; and
    analyzing the first digital image and the second digital image to determine a condition or disease of the iris.

2. The method of claim 1, further comprising placing a multi-spectral light source in contact with the skin directly adjacent to the portion of the eye.

3. The method of claim 1, wherein the first light beam and the second light beam are sequentially emitted.

4. The method of claim 1, wherein the first light beam comprises infrared light, and the first digital image is produced using only digitally captured infrared light.

5. The method of claim 1, further comprising automatically analyzing the digital image with a data processor.

6. The method of claim 1, further comprising identifying from the first digital image and the second digital image whether the eye has one of an eye disease or eye condition, wherein the one of an eye disease or eye condition is selected from the group consisting of pigment dispersion syndrome, iridociliary cysts, albinism, trauma, exfoliation syndrome, Fuchs' heterochromic iridocyclitis, problems caused by intraocular lens implants, and combinations thereof.

7. A method of detecting a condition or disease in an eye of a patient, the method comprising:
    emitting a light beam consisting essentially of infrared light into the eye through skin directly adjacent to a portion of the eye;
    digitally capturing infrared light penetrating an iris of the eye from the light beam within the eye;
    producing a digital image of the iris using only the digitally captured infrared light; and
    analyzing the digital image to determine a condition or disease of the iris.

8. The method according to claim 7, further comprising placing an infrared light source in contact with the skin directly adjacent to the portion of the eye.

9. The method according to claim 7, wherein the infrared light consists of a spectral range of infrared light concentrated around a first predetermined infrared wavelength.

10. The method of claim 7, further comprising:
    sequentially emitting into the eye through the skin more than one beam of infrared light, each of the more than one beam of infrared light having a light spectrum that is different from an other of the more than one beam of infrared;
    digitally capturing the infrared light penetrating the iris of the eye from within the eye for each of the more than one beam of infrared light; and
    producing a plurality of digital images of the eye, each of the plurality of digital images being produced from the light penetrating the iris from one of the more than one beam of infrared light.

11. The method of claim 7, further comprising automatically analyzing the digital image with a data processor.

12. The method of claim 7, further comprising identifying from the digital image whether the eye has one-of an eye disease or eye condition, wherein the one of an eye disease or eye condition is selected from the group consisting of pigment dispersion syndrome, iridociliary cysts, albinism, trauma, exfoliation syndrome, Fuchs' heterochromic iridocyclitis, problems caused by intraocular lens implants, and combinations thereof.

13. An apparatus for use in diagnostic imaging of an eye, comprising:

a body;

an infrared light source in combination with the body, wherein the infrared light source emits one or more spectral ranges of infrared light concentrated around a predetermined infrared wavelength;

the body including a light discharge end having a size and shape adapted to be placed against skin adjacent to and over a portion of the eye, wherein the light discharge end has a shape with a first dimension that is greater than a second dimension; and the body comprising at least one light focusing channel extending between the light discharge end and the infrared light source, the at least one light focusing channel including a reflective surface.

14. The apparatus according to claim 13, wherein the predetermined infrared wavelength is selected from wavelengths from about 650 nanometers to about 1000 nanometers.

15. The apparatus according to claim 13, wherein the shape of the light discharge end is rectangular, elliptical, or ovoidal.

16. The apparatus according to claim 13, wherein the infrared light source comprises:

a first light emitting diode that emits only a first spectral range of infrared light concentrated around a first predetermined infrared wavelength; and a second light emitting diode that emits only a second spectral range of infrared light concentrated around a second predetermined infrared wavelength, wherein the second predetermined infrared wavelength is different than the first predetermined infrared wavelength.

17. An apparatus for use in diagnostic imaging of an eye, comprising:

a body, the body including a light discharge end having a size and shape adapted to be placed against skin adjacent to and over a portion of the eye, wherein the light discharge end has a shape with a first dimension that is greater than a second dimension;

an infrared light source in combination with the body, wherein the infrared light source emits one or more spectral ranges of infrared light concentrated around a predetermined infrared wavelength;

a first light emitting diode that emits only a first spectral range of infrared light concentrated around a first predetermined infrared wavelength;

a second light emitting diode that emits only a second spectral range of infrared light concentrated around a second predetermined infrared wavelength, wherein the second predetermined infrared wavelength is different than the first predetermined infrared wavelength;

a first light focusing channel extending through the body and between the infrared light source and the light discharge end, wherein the first light emitting diode and the second light emitting diode are disposed in light discharging alignment with the first light focusing channel;

a second light focusing channel extending through the body and between the infrared light source and the light discharge end;

a third light emitting diode that emits only the first spectral range of infrared light concentrated around the first predetermined infrared wavelength; and a fourth light emitting diode that emits only the second spectral range of infrared light concentrated around the second predetermined infrared wavelength;

wherein the third light emitting diode and the fourth light emitting diode are disposed in light discharging alignment with the second light focusing channel.

18. The apparatus according to claim 13, further comprising:

a digital image detector;

a control device in activating combination with the digital image detector;

a recordable medium in combination with the digital image detector; and a user interface including a view screen in combination with at least one of the digital image detector and the recordable medium.

19. The apparatus according to claim 18, further comprising a constriction light source for creating consensual papillary constriction in the eye.

20. The method of claim 1, further comprising creating a consensual constriction in the eye using a further light source directed at the patient.

21. The method of claim 7, further comprising creating a consensual constriction in the eye using a further light source directed at the patient.

* * * * *

UNITED STATES PATENT AND TRADEMARK OFFICE
CERTIFICATE OF CORRECTION

| | | |
|---|---|---|
| PATENT NO. | : 7,712,901 B2 | Page 1 of 1 |
| APPLICATION NO. | : 11/999529 | |
| DATED | : May 11, 2010 | |
| INVENTOR(S) | : Miles N. Wernick et al. | |

It is certified that error appears in the above-identified patent and that said Letters Patent is hereby corrected as shown below:

Column 1, line 14, after the paragraph describing the Cross Reference to Related Application, please insert the following header and paragraph:

-- GOVERNMENT RIGHTS

This invention was made with government support under grant number EY015604 awarded by the National Eye Institute of the National Institutes of Health. The government has certain rights in the invention. --

Signed and Sealed this

Seventh Day of December, 2010

David J. Kappos
*Director of the United States Patent and Trademark Office*